United States Patent [19]

Eggler et al.

[11] Patent Number: 5,698,550
[45] Date of Patent: Dec. 16, 1997

[54] TETRALIN AND CHROMAN DERIVATIVES USEFUL IN THE TREATMENT OF ASTHMA, ARTHRITIS AND RELATED DISEASES

[75] Inventors: James F. Eggler, Stonington; Anthony Marfat, Mystic; Lawrence S. Melvin, Jr., Ledyard, all of Conn.

[73] Assignee: Pfizer Inc., New York, N.Y.

[21] Appl. No.: 920,291

[22] Filed: Jun. 14, 1993

[51] Int. Cl.$^6$ .......................... A61K 31/55; A61K 31/47; C07D 405/12; C07D 405/14

[52] U.S. Cl. .......... 514/212; 514/290; 514/291; 514/299; 514/302; 514/309; 514/249; 514/274; 514/312; 514/332; 514/333; 514/334; 514/335; 514/337; 514/338; 514/345; 514/348; 540/597; 544/126; 544/128; 544/131; 544/316; 544/354; 546/79; 546/89; 546/90; 546/101; 546/110; 546/115; 546/153; 546/155; 546/157; 546/194; 546/255; 546/256; 546/271.1; 546/271.7; 546/270.1; 546/280.1; 546/283.1; 546/290; 546/296; 546/301; 546/302; 546/303

[58] Field of Search .......................... 546/153, 155, 546/157, 255–256, 269, 272–274, 290, 296, 301–303, 89, 79, 90, 110, 115, 101, 194; 514/312, 332, 333, 334, 335, 337, 345, 348, 290, 291, 299, 302, 309; 540/597; 544/126, 128, 131

[56] References Cited

U.S. PATENT DOCUMENTS

| | | | |
|---|---|---|---|
| 4,625,034 | 11/1986 | Neiss et al. | 546/152 |
| 4,661,596 | 4/1987 | Kreft, III et al. | 546/152 |
| 4,680,404 | 7/1987 | Eggler et al. | 546/269 |
| 5,059,609 | 10/1991 | Eggler et al. | 514/314 |
| 5,296,486 | 3/1994 | Lazer et al. | 514/333 |
| 5,298,512 | 3/1994 | Eggler et al. | 514/314 |
| 5,384,318 | 1/1995 | Eggler et al. | 514/212 |
| 5,574,049 | 11/1996 | Manley | 546/256 |

FOREIGN PATENT DOCUMENTS

| | | |
|---|---|---|
| 0288962 | 11/1988 | European Pat. Off. . |
| 0313295 | 4/1989 | European Pat. Off. . |

OTHER PUBLICATIONS

Design of Prodrugs by Hans Bundgaard (Editor), pp. 1–92 (1985).
Sinkula et al, *Journal of Pharmaceutical Sciences* 64, pp. 181–210 (1975).
Shaw et al, *J. Med. Chem.* 34 pp. 1235–1242 (1991).
Musser et al, *J. Med. Chem.* 35 pp. 2501–2524 (1992).

*Primary Examiner*—Emily Bernhardt
*Attorney, Agent, or Firm*—Peter C. Richardson; Gregg C. Benson; James T. Jones

[57] ABSTRACT

Compounds of the formula

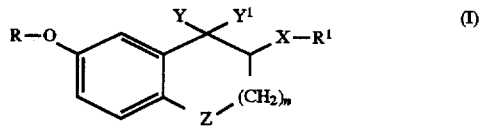

wherein

R is an optionally substituted heteroaryl group such as 2-chromanyl, 2-pyridyl or 5-fluoro-2-benzothiazoyl;

X is O, S or $(CH_2)_m$;

$R^1$ is phenyl or pyridyl, optionally substituted by one or more $(C_1-C_3)$alkyl, $(C_1-C_3)$alkoxy, carboxy or $[(C_1-C_3)$alkoxy]carbonyl groups;

n is 0, 1 or 2;

m is 1 or 2;

Y and $Y^1$ are taken together and are oxygen, or Y and $Y^1$ are taken separately, Y is hydrogen and $Y^1$ is hydroxy or an in vivo hydrolyzable acyloxy group;

Z is $CH_2$, $NR^2$, O or S; and $R^2$ is hydrogen or $(C_1-C_3)$alkyl;

are useful in the treatment of asthma, arthritis and related diseases mediated by leukotrienes.

17 Claims, No Drawings

TETRALIN AND CHROMAN DERIVATIVES USEFUL IN THE TREATMENT OF ASTHMA, ARTHRITIS AND RELATED DISEASES

This is a National Phase filing under 35 USC §371 based on PCT/US90/00692 which was filed internationally on Feb. 7, 1990.

BACKGROUND OF THE INVENTION

The present invention is directed to substituted tetralins, chromans and related compounds of the formula (I), depicted below, which by inhibiting 5-lipoxygenase enzyme and/or antagonizing PAF (platelet activating factor) are useful in the prevention or treatment of asthma, arthritis, psoriasis, ulcers, myocardial infarction, stroke and related disease states in mammals. The present invention is also directed to pharmaceutical compositions, and to a method of treating arthritis, asthma and related diseases.

Kreft et al., in U.S. Pat. No. 4,661,596, describe similarly active compounds which are disubstituted naphthalenes, dihydronaphthalenes or tetralins having the formula

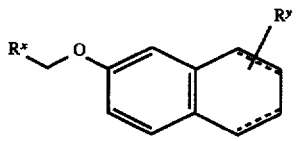

wherein the dotted lines represent optional double bonds, $R^x$ is 2-pyridyl, 2-quinolyl, 2-pyrazinyl, 2-quinoxalinyl, 2-thiazolyl, 2-benzothiazolyl, 2-oxazolyl, 2-benzoxazolyl, 1-alkyl-2-imidazolyl or 1-alkyl-2-benzimidazolyl and $R^y$ is hydroxy, lower alkoxy, lower alkyl or perfluoro alkyl. Eggler et al., in published European patent application number 313,295, have described similarly active compounds, including tetralins and chromans of the formula

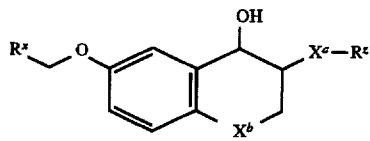

wherein $R^x$ is substantially defined as above, $R^z$ is aryl or heteroaryl, and $X^a$ and $X^b$ are, for example, oxygen or $CH_2$.

The chemical nomenclature employed herein generally follows that of "I.U.P.A.C. Nomenclature of Organic Chemistry, 1979 Edition," Pergammon Press, New York, 1979.

SUMMARY OF THE INVENTION

The present invention is directed to compounds having the structural formula

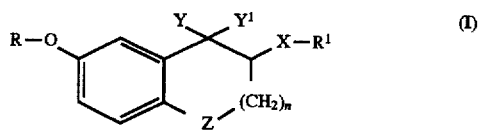

wherein

R is 2- or 4-pyridyl, 2- or 4-quinolyl, 1- or 3-isoquinolyl, 3- or 4-pyridazinyl, 3- or 4-cinnolinyl, 1-phthalazinyl, 2- or 4-pyrimidinyl, 2- or 4-quinazolinyl, 2-pyrazinyl, 2-quinoxalinyl, 1- or 3-indolizinyl, 2- or 4-oxazolyl, 2-benzoxazolyl, 3- or 5-isoxazolyl, 3-benzo[d] isoxazolyl, 2- or 4-thiazolyl, 2-benzothiazolyl, 3- or 5-isothiazolyl, 3-benzo[d]isothiazolyl, 1-[($C_1$–$C_4$) alkyl]-2- or 4-imidazolyl, 1-[($C_1$–$C_4$)alkyl]-2-benzimidazolyl, 1-[($C_1$–$C_4$)alkyl]-3- or 5-pyrazolyl or 1-[($C_1$–$C_4$)alkyl]-3(1H)-indazolyl; or one of said groups mono- or disubstituted on carbon with the same or different substituents which are bromo, chloro, fluoro, ($C_1$–$C_4$)alkyl, trifluoromethyl, phenyl, hydroxy, hydroxymethyl or ($C_1$–$C_4$)alkoxy, or on adjacent carbons with trimethylene, tetramethylene, —$CH_2$—O—$CH_2$— or —O—$CH_2$—O—;

X is O, S or $(CH_2)_m$;

$R^1$ is phenyl or pyridyl, or phenyl or pyridyl substituted by one or more ($C_1$–$C_3$)alkyl, ($C_1$–$C_3$)alkoxy, chloro, fluoro, carboxy or [($C_1$–$C_3$)alkoxy]carbonyl;

n is 0, 1 or 2;

m is 1 or 2;

Y and $Y^1$ are taken together and are oxygen (forming a carbonyl group), or Y and $Y^1$ are taken separately, Y is hydrogen, and $Y^1$ is hydroxy or an acyloxy group which is hydrolyzed to form a hydroxy group under physiological conditions;

Z is $CH_2$, $NR^2$, O or S; and $R^2$ is hydrogen or ($C_1$–$C_3$)alkyl;

a pharmaceutically acceptable acid addition salt thereof; or a pharmaceutically acceptable cationic salt when the compound contains a carboxy group.

For ease of preparation and their valuable biological activity, the more preferred compounds of the formula (I) are racemic or optically active compounds having the relative stereochemical formula

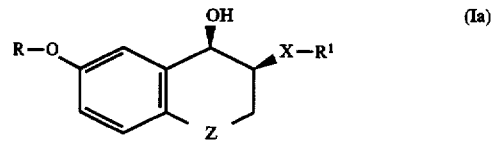

Most preferred are those compounds wherein R is 2-pyridyl or 2-quinolyl, $R^1$ is 3-pyridyl, Z is O and n is 1.

Said pharmaceutically-acceptable acid addition salts include, but are not limited to, those with HCl, HBr, $HNO_3$, $H_2SO_4$, $H_3PO_4$, $CH_3SO_3H$, p—$CH_3C_6H_4SO_3H$, $CH_3CO_2H$, gluconic acid, tartaric acid, maleic acid and succinic acid. In the case of those compounds of the formula (I) which contain a further basic nitrogen, it will, of course, be possible to form diacid addition salts (e.g., the dihydrochloride) as well as the usual monoacid addition salt. Said pharmaceutically-acceptable cationic salts include, but are not limited to, those of sodium, potassium, calcium, magnesium, ammonia, N,N'-dibenzylethylenediamine, N-methylglucamine (meglumine), ethanolamine and diethanolamine.

The reference to $Y^1$ as an acyloxy group which is hydrolyzed to a hydroxy group under physiological conditions refers to esters of a type which are frequently referred to as "pro-drugs." Such esters are now as well-known and common in the medicinal art as pharmaceutically-acceptable salts. Such esters are generally used to enhance oral absorption, but in any event are readily hydrolyzed in vivo to the parent hydroxy compound. The more preferred acyloxy groups are those in which the acyl moiety is the alpha-aminoacyl residue of a naturally occurring L-alpha-amino acid,

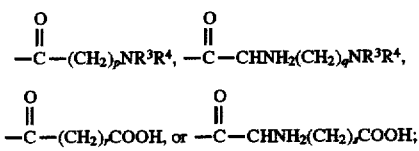

wherein
R³ and R⁴ are taken separately and are each independently hydrogen or $(C_1-C_4)$alkyl, or R³ and R⁴ are taken together with the nitrogen to which they are attached to form a pyrrolidine, piperidine, perhydroazepin or morpholine ring;
p is an integer from 1 to 4;
q is an integer from 1 to 3;
r is an integer from 2 to 3; and
s is an integer from 1 to 3.

Also forming a part of the present invention are pharmaceutical compositions for administration to a mammal which comprise a compound of the formula (I) and a pharmaceutically acceptable carrier; and a method of inhibiting 5-lipoxygenase enzyme and/or antagonizing PAF (platelet activating factor) in a mammal, particularly in man, so as to prevent or treat asthma, arthritis, psoriasis, gastrointestinal ulcers, stroke or myocardial infarction.

DETAILED DESCRIPTION OF THE INVENTION

The present invention is readily carried out. Thus, the compounds of the formula (I) wherein $Y^1$=OH, or Y and $Y^1$ form a carbonyl group, are prepared by conventional reaction of the corresponding phenol of the formula

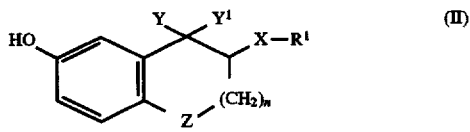

wherein R¹, X, Z and n are as defined above, with a compound of the formula $RX^1$, wherein R is as defined above and $X^1$ is a displacable group such as a halide (preferably chloride) in the presence of substantially one molar equivalent of a base which is sufficiently basic to convert the phenol to the phenolate. Preferred bases are such as NaH which irreversibly convert the phenol to the phenolate. The reaction is generally carried out in a reaction-inert solvent such as dimethylformamide, at elevated temperature (e.g., 70°–120° C.) until the reaction is substantially complete. If desired, an excess of $RX^1$ can be used in order to force the reaction to completion within a shorter time period.

As used here and elsewhere herein, the expression "reaction-inert solvent" refers to a solvent which does not interact with starting materials, reagents, intermediates or products in a manner which adversely affects the yield of the desired product.

The starting phenols of the formula (II) are readily available according to methods detailed by Eggler et al. in the published European application cited above. The cis-isomers (e.g., Ia) are generally preferred over corresponding trans-isomers. Fortunately, it is the preferred cis-isomer which usually predominates (sometimes with virtual exclusion of the trans-isomer) in the synthetic methods employed in preparation of the intermediate phenol compounds (II).

The heteroaryl halides and sulfonates ($RX^1$), which are required as starting materials for the present invention are readily available. Those compounds which are not articles of commerce, or known in the prior art, are readily prepared from known compounds using conventional chemical processes, as for example:

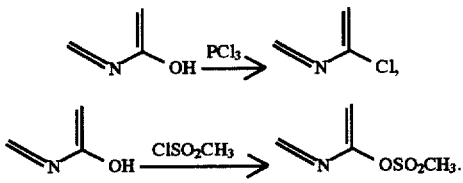

When the compound of the formula (I) contains a carboxy group, the final chemical step can be conventional hydrolysis of the corresponding lower alkyl ester, as exemplified below.

The prodrug esters of the present invention are prepared by conventional methods. Esters with alpha-amino acids, including natural L-amino acids, are generally prepared from the appropriate amino acid in which the alpha-amino group, substituent $NH_2$ or NH groups (e.g., lysine, ornithine, arginine, histidine, tryptophan), hydroxy groups (serine, homoserine, threonine, tyrosine), mercapto groups (cysteine) and carboxy groups (glutamic acid, aspartic acid) are in protected form, e.g., N-benzyloxycarbonyl, O- and S-benzyl, with removal of the protecting group by conventioanl catalytic hydrogenation in a subsequent step. Similarly, in the case of esters with primary or secondary amino substituents, the acids will be coupled with amino groups protected. Such protection is, of course, unnecessary with those acids containing tertiary amino substituents. Finally, the carboxy substituted esters are most conveniently prepared from the cyclic anhydride:

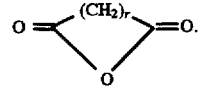

The hydroxy compounds of the formula (I) wherein Y is OH contain two such asymmetric carbons—corresponding to two racemates and four optically active compounds. One of these racemates is the above noted cis-isomer, and the other the trans-isomer. Each of these racemates is capable of resolution into a pair of enantiomers via diastereomeric salts, as detailed in the preceding paragraph. It is preferred, however, to convert the racemic alcohol to corresponding diastereomeric esters or urethanes formed with an optically active acid or isocyanate. Such covalently bonded derivatives are generally subjectable to a broader variety of separation methods (e.g., chromatography) than are diastereomeric salts. Such diastereomeric esters are formed from the alcohol and the optically active acid by standard methods, generally those involving activation of the acid, e.g., as the acid chloride, as a mixed anhydride with an alkyl chloroformate, or with a dehydrative coupling agent such as dicyclohexylcarbodiimide. A preferred optically active acid in the present case is $N^{alpha}$-(t-butoxy)tryptophan. Once the resulting diastereomeric esters are separated, e.g., by chromatographic methods, they are hydrolyzed by conventional methods, e.g., aqueous acid or aqueous base, to obtain the enantiomeric, optically active alcohols.

Concerning the biological activity of the present compounds, it is known that arachidonic acid is metabolized in mammals by means of two distinct pathways, one leading to prostaglandins and thromboxanes, the other to several oxidative products called leukotrienes, which are designated by letter number combinations such as B4, C4, D4 and E4. The first step in this oxidative pathway is the oxidation of arachidonic acid under the influence of 5-lipoxygenase enzyme, an enzyme which is generally inhibited by the compounds (I) of the present invention, thus blocking the synthesis of all leukotrienes. That in itself provides the mechanism sufficient for the utility of the present compounds in the treatment or prevention of asthma (where $LTC_4$ and LTD4 are understood to be mediators), arthritis (where LTB4 is understood to be a mediator in inflammation), psoriasis (where LTB4 is understood to be a mediator), ulcers (where $LTC_4$ and LTD4 are understood to be mediators) and myocardial infarction (where LTB4 is understood to be a mediator).

The in vitro activity of the compounds of the formula (I) as inhibitors of 5-lipoxygenase enzyme is tested as follows. RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed 1 time with RPMI 1640 (GIBCO) and resuspended in RPMI 1640 plus 1 microM glutathione to a cell density of $1\times10^7$ cells/ml. A volume of 0.5 ml of the cell suspension is incubated at 30° C. with 0.001 ml of dimethylsulfoxide solution of drug for 10 minutes. The reaction is started by a simultaneous addition of 0.005 ml (14C)-arachidonic acid in ethanol and 0.002 ml A23187 in dimethylsulfoxide to give final concentrations of 5.0 and 7.6 microM, respectively. After a 5 minute incubation at 30° C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent system of acetonitrile/$H_2O$/acetic acid (0.1%) with a linear acetonitrile gradient from 35% to 70% over 15 minutes at 1 ml/minute. Quantitation is accomplished with a Berthold Radioactivity Monitor equipped with a built-in integrator and a 0.2 ml flow cell mixing 2.4 ml/minute Omnifluor (NEN) with column effluent. Integration units for each product are calculated as a percentage of total integration units, and then compared to the average control levels. The results are expressed as "Percent of Control" and are plotted vs the log of drug concentration. The $IC_{50}$ values are estimated by graphical inspection.

The compounds of the formula (I) are tested for PAF (platelet activating factor) antagonism in vitro by testing their ability to compete with radiolabelled PAF for specific PAF receptor sites on rabbit platelet homogenate. A rabbit blood mixture (500 ml) is purchased from Rockland, Inc., Gilbertsville, Pa. The blood mixture is 4 parts blood:1 part 4% sodium citrate (v/v), and is obtained by heart puncture from normal, approximately 8-month old New Zealand white rabbits. The blood mixture is delivered overnight on wet ice (approx. 8° C.). The blood mixture is centrifuged at 514 G for 10 minutes. The supernatant platelet-rich plasma is gently laid over Ficoll-Pague (Pharmacia) at a ratio of 9 parts plasma: 2 parts Ficoll (v/v). The plasma/Ficoll mixture is centrifuged at 856 G for 20 minutes. Located at the interface of the plasma and Ficoll layers, the platelet layer is collected and washed in a buffer containing 150 mM NaCl, 10 mM Tris and 1 mM EDTA (pH 7.5). The mixture is centrifuged at 1926 G for 25 minutes. The resulting pellet is resuspended in the NaCl/Tris/EDTA buffer and centrifuged again (1926 G, 25 minutes). This time the pellet is resuspended in a sodium-free buffer (10 mM Tris, 1 mM EDTA, 5 mM $MgCl_2$ (pH 7.5)) and centrifuged at 1926 G for 25 minutes. The platelet pellet is resuspended in about 10 ml of sodium-free buffer. This suspension is quick-frozen in methanol/dry ice bath and thawed quickly three times before being frozen again for storage in 1 ml aliquots at −70° C. Protein concentration of the suspension is determined by a Bio-Rad assay.

Assay Conditions: Note: All concentrations given are FINAL concentrations in 250 µl.

The following are added to a 12×75 mm polystyrene tube:
(1) 5 µl of one of the following:
A. DMSO (to determine total binding)
B. 1 µM PAF (to determine non-specific binding)
C. 30 nM–100 µM compound in DMSO
(2) 25 µl 3H-PAF (specific activity 30–60 Ci/mmol) in sodium-free buffer +0.25% bovine serum albumin (BSA) (Approx. 10.000 cpm/25µ)
(3) 220 µl homogenate preparation (0.1 mg/ml) in sodium-free buffer +0.25% BSA.

The reaciton tubes are incubated at 25° C. for 45 minutes. Four ml of cold sodium-free buffer+0.25% BSA are added to each tube. The contents are quickly filtered through a Whatman GF/C filter with a Yeda separation device. The filter is washed 3 times with 4 ml sodium-free/BSA buffer. The filter is transferred to a scintillation vial. Ultrafluor scintillation fluid is added. The vial is capped, vortexed and counted for 3H.

Date Calculation and Analysis:

Percent specific binding is calculated using the formula:

$$\% \ SB = (X-NSB)/(TB-NSB),$$

where
X=cpm sample
NSB=cpm non-specific binding
TB=cpm total binding

Percent specific binding is graphed as a function of compound concentration. $IC_{50}$ is that concentration at which 50% SB occurs. Alternatively, the $IC_{50}$ is calculated using the logistic dose-response (Hill plot) option of the VAX Biostat utility. The inhibitory constant (Ki) is calculated by using the formula:

$$Ki=(IC_{50})/[1+(L/Kd)],$$

where
L=concentration of ligand added
(nM)=cpm added/cpm of 1 nM 3H-PAF
Kd=0.83 nM (dissociation constant)

To evaluate the compounds of the formula (I) in vivo, they are tested by the so-called PAF lethality assay procedure:

Materials

Mice: CD1 males, all approximately the same weight (approximately 26 grams), 12 per group.

Vehicle for oral drug dosing: EES (5% ethanol, 5% emulphor, 90% saline). Stored at room temperature.

Drugs: For routine screening at 50 mg/kg, 20 mg drug is dissolved in 4 ml EES, using sonication in a sonicator bath or grinding in a Ten Broeck grinder to dissolve drug if necessary. If solubility is still a problem, the drug is used as a suspension.

Vehicle for i.v. Injection: Saline with 2.5 mg/ml Bovine Serum Albumin (BSA, Sigma #A4378) and 0.05 mg/ml Propranolol (Sigma #P0884). Prepared fresh daily and kept at room temperature.

Platelet Activating Factor (PAF): A 10 microM stock solution is prepared by dissolving 1 mg PAF (Calbiochem #429460) in 0.18 ml ethanol. This is stored at −20° C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.

Positive Control: Phenidone is used at 25 mg/kg (its approximate ED 50).

Method:

45 minutes before PAF injection, mice are treated orally with drug using 0.1 ml/10 grams body weight. 35 to 40 minutes later they are placed under a heat lamp to dilate the caudal vein for PAF injection. PAF is injected i.v. at 0.1 ml/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided.

Variations

1. The time for oral dosing can be changed.
2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

Compounds of the present invention are tested for utility against stroke in gerbils, according to the method of Gaudet et al., Stroke, vol. 11, pp. 648–652 (1980).

For use in the prevention or treatment of asthma, arthritis, psoriasis, gastrointestinal ulcers myocardial infarction and stroke in a mammal, including man, a compound of the formula (I) is given in a 5-lipoxygenase inhibiting/PAF antagonistic amount of about 0.5–50 mg/kg/day, in single or divided daily doses. A more preferred dosage range is 2–20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1 cis-3-(3-Pyridylmethyl)-6-(2-quinolyloxy)-4-chromanol 3-(3-Pyridylmethyl)-4,6-chromandiol (5.0 g, 19.4 mmol; EP appln. 312,295) was dissolved in 100 ml dimethylformamide. 2-Chloroquinoline (3.17 g, 19.4 mmol) and then NaH (0.98 g of a 50% dispersion in oil, 20.4 mmol) were added and the mixture stirred at 90°–95° C. for 16 hours. The reaction mixture was cooled, quenched into 500 ml $H_2O$, and extracted 4×400 ml ethyl acetate. The organic layers were combined, washed 3×400 ml $H_2O$ and 1×400 ml brine, dried ($Na_2SO_4$), stripped to an oil (9.47 g) and chromatographed in silica gel gradiently eluted with 4–15% $CH_3OH$ in $CH_2Cl_2$ to yield 5.07 g of present title product as a white foam; IR (KBr) 3190, 1602, 1492 $cm^{-1}$; MS 384 ($M^+$).

EXAMPLE 2 cis-3-(3-Pyridylmethyl)-6-(2-quinolyloxy)-4-chromanol Dihydrochloride

Title product of the preceding Example (161 mg, 0.42 mmol) was dissolved in 10 ml of 1:1 ethyl acetate:ether. 1N HCl in ether (1.1 ml, 1.05 mmol) was added and, after stirring for 2 hours under $N_2$, the mixture was stripped to yield 193 mg of title product; mp 150° C. (dec.), after shrinking and gumming at 130°–135° C.; HRMS calcd. 384.1475, found 384.1474.

EXAMPLE 3

(+)- and (−)-cis-3-(3-Pyridylmethyl)-6-(2-quinolyloxy)-4-chromanol

Title product of Example 1 (4.96 g, 12.9 mmol), N-(t-butoxycarbonyl)-L-tryptamine (4.50 g, 15.5 mmol), 4-dimethylaminopyridine (1.89 g, 15.5 mmol) and dicyclohexylcarbodiimide (3.20 g, 15.5 mmol) were combined in 60 ml $CH_2Cl_2$ and stirred under $N_2$ for 16 hours. Dicyclohexylurea was recovered by filtration, the mother liquor stripped to 11.6 g of dry foam, and the foam chromatographed on silica gel using 3% $CH_3OH$ in $CH_2Cl_2$ for elution to yield 1.32 g of the less polar diastereomeric ester, 3.57 g of mixed (primarily less polar) esters suitable for chromatographic recycling, and 4.58 g of the more polar diastereomeric ester.

The less polar diasteroisomer (1.10 g) was stirred in 40 ml of methanol and 20 ml of 1N NaOH for 40 minutes, stripped of methanol, and crude (−)-title product recovered by filtration. The wet cake was taken up in 150 ml ethyl acetate, washed 2×100 ml 1N NaOH and 1×100 ml brine, dried ($Na_2SO_4$), stripped and the residue triturated with hexane to yield (−)-title product as a white solid, 0.57 g; mp 113°–115° C.; $[alpha]_D$=+150° C. (c=1.56 in $CH_3OH$); IR($CHCl_3$) 1621, 1603, 1490 $cm^{-1}$.

The more polar diastereoisomer, 3.49 g was hydrolyzed in like-manner to yield (+)-title product, 1.72 g; having identical physical properties except for sign of rotation.

EXAMPLE 4 cis-3-(3-Pyridylmethyl)-6-(2-pyridyloxy)-4-chromanol

By the method of Example 1, 2-chloropyridine and 3-(3-pyridylmethyl)-4,6-chromandiol were converted to present title product in like yield; mp 67°–68° C.; IR($CHCl_3$) 1598; 1491 $cm^{-1}$.

EXAMPLE 5 cis-3-(3-Pyridyloxy)-6-(2-quinolyloxy)-4-chromanol

By the method of Example 1, 2-chloroquinoline and 3-(3-pyridyloxy)-4,6-chromandiol (EP appln. 312,295) were converted to present title product in like yield; mp 112°–114° C.; IR (CHCl₃) 3563, 1620, 1603 cm⁻¹.

EXAMPLE 6

By the method of Example 1, the following additional compounds are prepared from the appropriately substituted 4,6-chromandiol, 2,3,4,5-tetrahydro-1-benzoxepin-5,7-diol, 1,7-naphthalenediol, or 1,6-indanediol (EP appln. 312,295):

trans-3-(3-Pyridylmethyl)-6-(2-quinolyloxy)-4-chromanol;
cis-3-Phenoxy-6-(2-quinolyloxy)-4-chromanol;
cis-3-(4-Methoxyphenoxy)-6-(2-quinolyloxy)-4-chromanol;
cis-3-(3-Methoxyphenoxy)-6-(2-quinolyloxy)-4-chromano;
cis-2,3,4,5-Tetrahydro-4-phenoxy-7-(2-quinolyloxy)-1-benzoxepin-5-ol;
trans-2,3,4,5-Tetrahydro-4-phenoxy-7-(2-quinolyloxy)-1-benzoxepin-5-ol;
cis-2,3,4,5-Tetrahydro-4-(3-pyridyloxy)-7-(2-quinolyloxy)-1-benzoxepin-5-ol;
cis-2,3,4,5-Tetrahydro-4-(3-(methoxycarbonyl)phenoxy)-7-(2-quinolyloxy)-1-benzoxepin-5-ol;
cis-3-(3-Methoxycarbonyl)benzyl)-6-(2-quinolyloxy)-4-chromanol;
cis-3-(4-Methoxy-3-(methoxycarbonyl)benzyl-6-(2-quinolyloxy)-4-chromanol;
cis-2-Benzyl-1,2,3,4-tetrahydro-7-(2-quinolyloxy)-1-naphthol;
cis-2-Benzyl-6-(2-quinolyloxy)-1-indanol;
cis-2-Phenoxy-1,2,3,4-tetrahydro-7-(2-quinolyloxy)-1-naphthol;
cis-3-Benzyl-6-(2-quinolyloxy)thiochroman-4-ol.

EXAMPLE 7 cis-2,3,4,5-Tetrahydro-4-(3-carboxyphenoxy)-7-(2-quinolyloxy)-1-benzoxepin-5-ol

The corresponding methyl ester of the preceding Example (1.3 g) is combined with a mixture of methanol (100 ml) and 5N NaOH (10 ml), stirred at 90°–95° C. for 10 minutes, then stripped of methanol, the aqueous residue diluted with 10 ml of water, acidified to pH 5 and title product recovered by filtration.

In like manner, other ester products of the preceding Examples are converted to:

cis-3-(3-Carboxybenzyl)-6-(2-quinolyloxy)-4-chromanol; and
cis-3-(3-Carboxy-4-methoxybenzyl)-6-(2-quinolyloxy)-4-chromanol.

EXAMPLE 8

By the method of Example 1, the following additional compounds are prepared from the appropriately substituted heteroaryl chloride:

cis-3-(3-Pyridylmethyl)-6-(5-fluoro-2-benzothiazolyloxy)-4-chromanol;
cis-3-(3-Pyridylmethyl-6-(4-pyridyloxy)-4-chromanol;
cis-3-(3-Pyridylmethyl)-6-(2-pyrimidinyloxy)-4-chromanol;
cis-3-(3-Pyridylmethyl)-6-(2-quinoxalinyloxy)-4-chromanol;
cis-3-(3-Pyridylmethyl)-6-(2-benzoxazoyl)-4-chromanol; and
cis-3-(3-Pyridylmethyl)-6-(3-isothiazolyl)-4-chromanol.

EXAMPLE 9

By the method of Example 1, the following additional compounds are prepared from the appropriately substituted 6-hydroxy-4-chromanone, 2,3-dihydro-6-hydroxy-4(1H)-quinolone, or 7-hydroxy-3,4-dihydro-1(2H)-naphthalenone (EP appln. 312,295):

2-Benzyl-3,4-dihydro-7-(2-quinolyloxy)-1(2H)-naphthalenone;
3,4-dihydro-2-(2-phenylethyl)-7-(2-quinolyoxy)-1(2H)-naphthalenone;
3-Benzyl-2,3-dihydro-6-(2-quinolyloxy)-4(1H)-quinolone; and
3-(2-pyridylmethyl)-6-(2-quinolyloxy)-4-chromanone.

We claim:

1. A compound having the structural formula

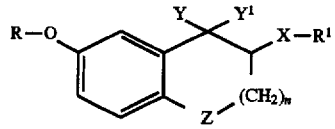

wherein

R is 2- or 4-pyridyl or 2- or 4-quinolyl; or one of said groups is mono- or disubstituted on carbon with the same or different substituents which are bromo, chloro, fluoro, ($C_1$–$C_4$)alkyl, trifluoromethyl, phenyl, hydroxy, hydroxymethyl or ($C_1$–$C_4$)alkoxy, or on adjacent carbons with trimethylene, tetramethylene,
—$CH_2$—O—$CH_2$— or —O—$CH_2$—O—;

X is O, S or ($CH_2$)$_m$;

$R^1$ is phenyl or pyridyl, or phenyl or pyridyl substituted by one or more ($C_1$–$C_3$)alkyl, ($C_1$–$C_3$)alkoxy, chloro, fluoro, carboxy, or [($C_1$–$C_3$)alkoxyl]carbonyl n is 1;

m is 1 or 2;

Y and $Y^1$ are taken together and are oxygen, or Y and $Y^1$ are taken separately, Y is hydrogen and $Y^1$ is (a) hydroxy or (b) an ester group which attaches through its carbonyloxy and which is hydrolyzed to form $Y^1$ as a hydroxy group under physiological conditions; and Z is $CH_2$, O or S;

a pharmaceutically acceptable acid addition salt thereof; or a pharmaceutically acceptable cationic salt thereof when said compound contains a carboxy group.

2. A compound of claim 1 wherein Y and $Y^1$ are taken separately and $Y^1$ is a carbonyloxy group in which the carbonyl moiety is the alpha-aminocarbonyl residue of a naturally occurring L-alpha-amino acid,

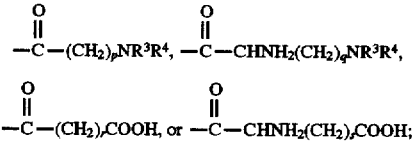

$R^3$ and $R^4$ are taken separately and are each independently hydrogen or ($C_1$–$C_4$)alkyl, or $R^3$ and $R^4$ are taken together with the nitrogen to which they are attached to form a pyrrolidine, piperidine, perhydroazepin or morpholine ring;

p is an integer from 1 to 4;

q is an integer from 1 to 3;

r is an integer from 2 to 3; and s is an integer from 1 to 3.

3. A compound of claim 1 wherein Y and $Y^1$ are taken separately and $Y^1$ is hydroxy.

4. A racemic or optically active compound of claim 3 having the relative stereochemical formula

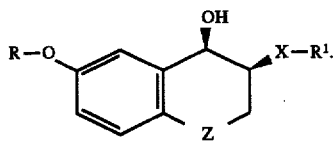

5. A compound of claim 4 wherein Z is O, X is $CH_2$ and $R^1$ is 3-pyridyl.

6. A compound of claim 4 wherein X is O.

7. The racemic compound of claim 6 wherein R is 2-quinolyl.

8. The racemic compound of claim 5 wherein R is 2-pyridyl.

9. The racemic compound of claim 5 wherein R is 2-quinolyl.

10. An optically active compound of claim 5 wherein R is 2-quinolyl.

11. A pharmaceutical composition for administration to a mammal which comprises a 5-lipoxygenase inhibiting or PAF antagonist amount of a compound of claim 1 and a pharamaceutically acceptable carrier.

12. A method of treating asthma, comprising administering an effective amount of a compound of claim 1 to a mammal in need of such treatment.

13. A method of treating arthritis, comprising administering an effective amount of a compound of claim 1 to a mammal in need of such treatment.

14. A method of treating psoriasis, comprising administering an effective amount of a compound of claim 1 to a mammal in need of such treatment.

15. A method of treating gastrointestinal ulcers, comprising administering an effective amount of a compound of claim 1 to a mammal in need of such treatment.

16. A method of treating myocardial infarction comprising administering an effective amount of a compound of claim 1 to a mammal in need of such treatment.

17. A method of treating stroke, comprising administering an effective amount of a compound of claim 1 to a mammal in need of such treatment.

* * * * *